(12) United States Patent
Kovtun et al.

(10) Patent No.: US 6,510,339 B2
(45) Date of Patent: Jan. 21, 2003

(54) ECG AUTO-GAIN CONTROL

(75) Inventors: Vladimir V. Kovtun, Eagan, MN (US); Paul D. Paulson, Chaska, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 237 days.

(21) Appl. No.: 09/731,520

(22) Filed: Dec. 6, 2000

(65) Prior Publication Data

US 2002/0099300 A1 Jul. 25, 2002

(51) Int. Cl.[7] ............................................. A61B 5/0402
(52) U.S. Cl. ........................ 600/509; 600/515; 128/903
(58) Field of Search ................................. 600/508, 509, 600/515, 516, 517, 518, 521, 523; 128/898, 901, 903, 904; 607/4, 5, 25, 27, 28, 32

(56) References Cited

U.S. PATENT DOCUMENTS

| | | | | |
|---|---|---|---|---|
| 5,107,833 A | * | 4/1992 | Barsness | 128/901 |
| 5,231,990 A | | 8/1993 | Gauglitz | 128/697 |
| 5,309,920 A | * | 5/1994 | Gallant et al. | 600/515 |
| 5,365,932 A | * | 11/1994 | Greenhut | 600/508 |
| 5,374,282 A | | 12/1994 | Nichols et al. | 607/18 |
| 5,458,621 A | * | 10/1995 | White et al. | 600/518 |
| 5,560,369 A | * | 10/1996 | McClure et al. | 600/517 |
| 5,620,466 A | | 4/1997 | Haefner et al. | 607/5 |
| 5,658,317 A | | 8/1997 | Haefner et al. | 670/5 |
| 5,662,688 A | | 9/1997 | Haefner et al. | 607/5 |
| 5,685,315 A | * | 11/1997 | McClure et al. | 600/521 |
| 5,745,531 A | | 4/1998 | Sawahashi et al. | 374/345 |
| 5,891,048 A | | 4/1999 | Nigam et al. | 600/521 |
| 6,038,435 A | | 3/2000 | Zhang | 455/234.1 |
| 6,041,250 A | | 3/2000 | Depinto | 600/509 |
| 6,106,481 A | * | 8/2000 | Cohen | 128/898 |

* cited by examiner

Primary Examiner—Willis R. Wolfe
(74) Attorney, Agent, or Firm—Nikolai & Mersereau, P.A.; Thomas J. Nikolai

(57) ABSTRACT

A method and apparatus for automatic gain control (AGC) method are provided to control the output from a medical device monitoring electrical potentials. The AGC method and apparatus accumulate data indicative of at least one vector in a cycle buffer, calculate an amplitude representative of the signal, compare the calculated value with a set of thresholds, and calculate an adjustment to the gain setting based on the amplitudes relationship to the thresholds.

8 Claims, 3 Drawing Sheets

ECG AUTO-GAIN CONTROL

BACKGROUND OF THE INVENTION

1. Field of the Invention

The present invention relates generally to an automatic gain control (AGC) apparatus and method for controlling the output from medical devices, and more particularly to an automatic gain control apparatus and method for control of the output from a multi-lead electrocardiogram device.

2. Description of the Related Art

Humans generate a variety of electrical impulses through nerve and muscular activity. Doctors frequently monitor selected impulses to diagnose diseases and otherwise evaluate a patient's health. Impulses from the heart and brain are most frequently monitored. In the case of the heart, electrocardiograms (ECGs) provide doctors with an indication of the heart's electrical activity in both the atria and the ventricles. Since the ECG is reflective of both atrial and ventricular activity, the ECG is particularly useful in evaluating a patient's cardiac rhythm and health.

ECG recordings are derived from electrodes placed on a patient's skin at predetermined locations about the patient's body. The signals picked up by the contacts create particular waveforms dependent upon the number of electrodes and their location on the body. A typical waveform associated with the ECG is the PQRST-complex. The excursions of the PQRST-complex represent the voltage difference at the body's surface sensed by the attached electrodes, typically twelve electrodes, relative to a reference electrode.

The PQRST-complex is indicative of both atrial and ventricular depolarization and repolarization events. The P-wave corresponds to the depolarization of the atria. Atrial depolarization is usually lasts about 0.1 second and has an amplitude of between 0.1 and 0.2 millivolt as sensed by an ECG. The interval of time from the beginning of the P-wave to the beginning of the QRS-complex is called the PR-interval. The PR-interval is normally no longer than 0.2 seconds. The QRS-complex corresponds to ventricular depolarization. Ventricular depolarization usually lasts about 0.08 to 0.10 second and has an amplitude of about 0.5 to 3.0 millivolt as sensed by the ECG. Thus, the QRS-complex typically has a larger amplitude than the P-wave. The increased amplitude is primarily due to the ventricle's greater muscle mass and the depolarization synchronization due to the ventricles' network of nerves. The ST-segment follows the completion of the QRS complex. The ST-segment is a segment of zero voltage. The segment corresponds to the action potential's refractory period when the ventricles remain depolarized. The ST-segment typically lasts about 0.15 second. The T-wave follows the ST-segment. The T-wave corresponds to ventricular repolarization. Repolarization is typically a slower process than depolarization and does not propagate from cell to cell as does depolarization. Thus, the T-wave is typically small in amplitude and lasts between about 0.15 and 0.20 second.

The waveform generated by the voltage changes over time are output as a continuous wave on a monitor or printed on a rhythm strip by the ECG. Doctors can evaluate anomalies in an ECG's output to diagnose diseases and evaluate a patient's overall health. To better enable comparison, the output from an ECG is governed by convention. Particularly, the ECG is configured to maintain the waveform's maximum amplitude between approximately 10 to 20 millimeters as printed or displayed. The printed rhythm strip typically includes a series of horizontal and vertical lines forming a grid. Typically, the lines are one millimeter apart. The horizontal lines represent voltage and, by convention, each line is indicative of a 0.1 millivolt change. The vertical lines represent time and, again by convention, each line is indicative of a 0.04 second interval. To standardize the output, the highest waves typically found in the QRS-complex are set at around 10 mm in height. This height, again set by convention, enables the direct comparison of different outputs. While monitoring a patient, the amplitude of the ECG's output can vary due to a number of physical and physiological changes not related to the condition of the heart. These changes can cause variations in the output not indicative of cardiac function, making interpretation by a physician more difficult. To compensate for these changes, ECG devices are typically equipped with a vertical gain control. The gain control typically requires the operator to switch between a plurality of pre-selected gains to bring the output of the ECG to the desired amplitude. The physician must review the output, determine the appropriate gain setting, and adjust the gain. The attention to the ECG's gain setting diverts the physician's attention away from the patient. Thus, a need exists for a method and apparatus that automatically adjust the gain settings on the ECG.

The present invention meets the above needs and provides additional advantages and improvements that will be evident to those skilled in the art upon review of the following description and figures.

SUMMARY OF THE INVENTION

The present invention provides an apparatus and method for automatic gain adjustment for an ECG's output. The present invention allows the monitoring of an ECG's output without affecting the ECG's normal processing. Further, the present invention provides an AGC that may be defeatable, allowing a user to switch between manual and automatic gain control.

The method includes receiving data from an ECG and using the data to determine an appropriate gain setting. Thus, the method first involves receiving data representative of at least one vector from an electrocardiogram device. The data indicative of the vector used by the automatic gain control may be decimated or only a fraction of the data used in determining the appropriate gain setting. The amplitude of the vector is then determined. The amplitude may be determined by comparing the amplitude of a particular vector to a baseline. The baseline being established by taking an average amplitude of the input vector over a period of time. Data above a particular exclusion threshold may be excluded from the baseline value to prevent the inclusion of aberrant data in the calculation. The amplitude may be determined for a particular vector during a measurement window. The measurement window may be initiated by the amplitude reaching or exceeding an initiation threshold. The amplitude of the vector is then compared to a plurality of thresholds. The particular thresholds reached or exceeded establish gain values used to determine the appropriate gain setting. The gain setting is then adjusted based on the gain values determined in the prior steps. The gain value may be input into an algorithm and the relationship between the gain values used to determine the gain setting.

The method of the present invention may be implemented in a device for auto-gain control. The specific components may be implemented through circuits, software or a combination of the two. The device includes at least one circle buffer for storing data indicative of output of an electrocardiograph device. A baseline is connected to the circle buffer to read the stored data. The detection circuit establishes a baseline or running average for the amplitude from the data. A maximum amplitude detection circuit determines the maximum amplitude from a particular set of data relative to the baseline. A comparator circuit compares a plurality of amplitudes from the maximum amplitude detection circuit with a plurality of thresholds to establish a set of gain values. The set of gain values are provided to a decision circuit for altering a gain setting for the output of the electrocardiograph device based on a relationship between set of gain values.

DETAILED DESCRIPTION OF THE INVENTION

Figure 1:
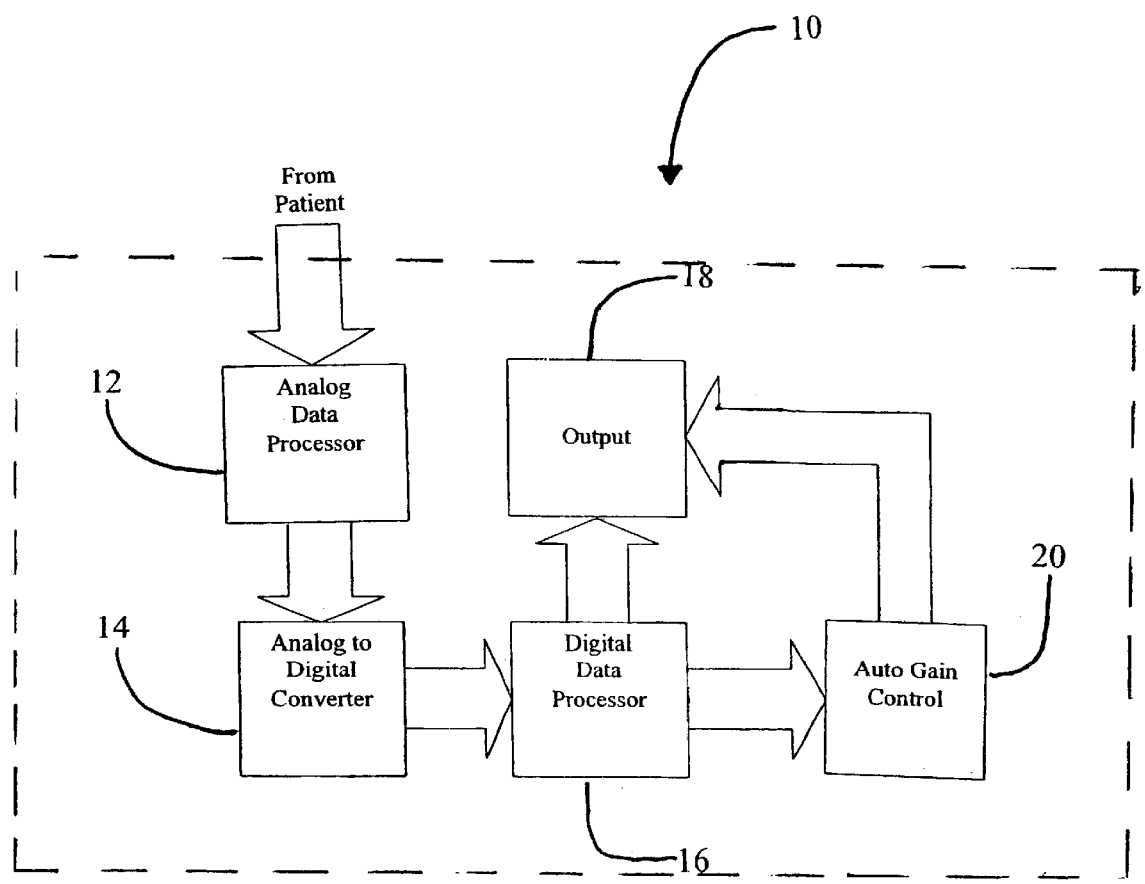
FIG. 1 is a block diagram illustrating an electrocardiograph including an automatic gain control in accordance with the present invention.

The present invention provides an apparatus and method to automatically control the gain applied to a medical device's output. The invention is applicable to a variety of medical devices used to detect electrical signals from a patient's body. The invention is described in the context of an electrocardiogram (ECG) as a specific example for illustrative purposes only. The appended claims are not intended to be limited to any specific example or embodiment in the following description. It will be understood by those skilled in the art that the present invention may be used in conjunction with a variety of medical devices, including, but not limited to ECGs. Further, in the drawings described below, the reference numerals are generally repeated where identical elements appear in more than one figure.

FIG. 1 illustrates an ECG device 10 in accordance with the present invention. The ECG device 10 includes an automatic gain control (AGC) 20. Typically, ECG 10 also includes an analog data processor 12, an analog to digital (A/D) converter 14, digital data processor 16, and an output device 18. The ECG is generally configured to produce an output indicative of the cardiac function of a patient, typically as a graphical recording. A plurality of leads, not shown, electrically connect ECG 10 to the patient. Typically, ECG device 10 includes from 1 to 12 leads. The leads sense the electrical potential at the skin surface resulting from depolarization and subsequent repolarization of the heart and transmit an analog signal indicative of the electrical potentials to ECG device 10.

The leads are typically connected to an analog data processor. Thus, analog data processor 12 receives the signals. Analog data processor 12 may include low voltage amplifiers and filters. After processing by analog data processor 12, the signal is typically sent to an analog to digital (A/D) converter 14. A/D converter 14 receives the signals from the analog processing circuit 12 and transforms the data into digital data. The digital data originating from an individual lead is typically referred to as a vector. Typically, 12 vectors are used to establish the typical ECG tracing. Each vector corresponds to the electrode on the particular lead feeding the signal to ECG device 10. Digital data processor 16 processes the vectors from the patient to produce a waveform indicative of the analog signals from the patient. The waveforms are then displayed by the output device 18. Typically, the output device 18 is in the form of a printed graph, a video display or in some other human or machine readable format. The output device's baseline is the point along the vertical axis representative of a zero potential. The output's amplitude is the difference between the output at any particular moment and the baseline and may be positive or negative. An AGC 20 monitors the amplitude of output 18 and adjusts the gain to keep the maximum amplitudes within a certain range. The gain is the multiplication factor by which the amplitude is multiplied to keep the output within a desired range on the screen or printout.

Figure 2:
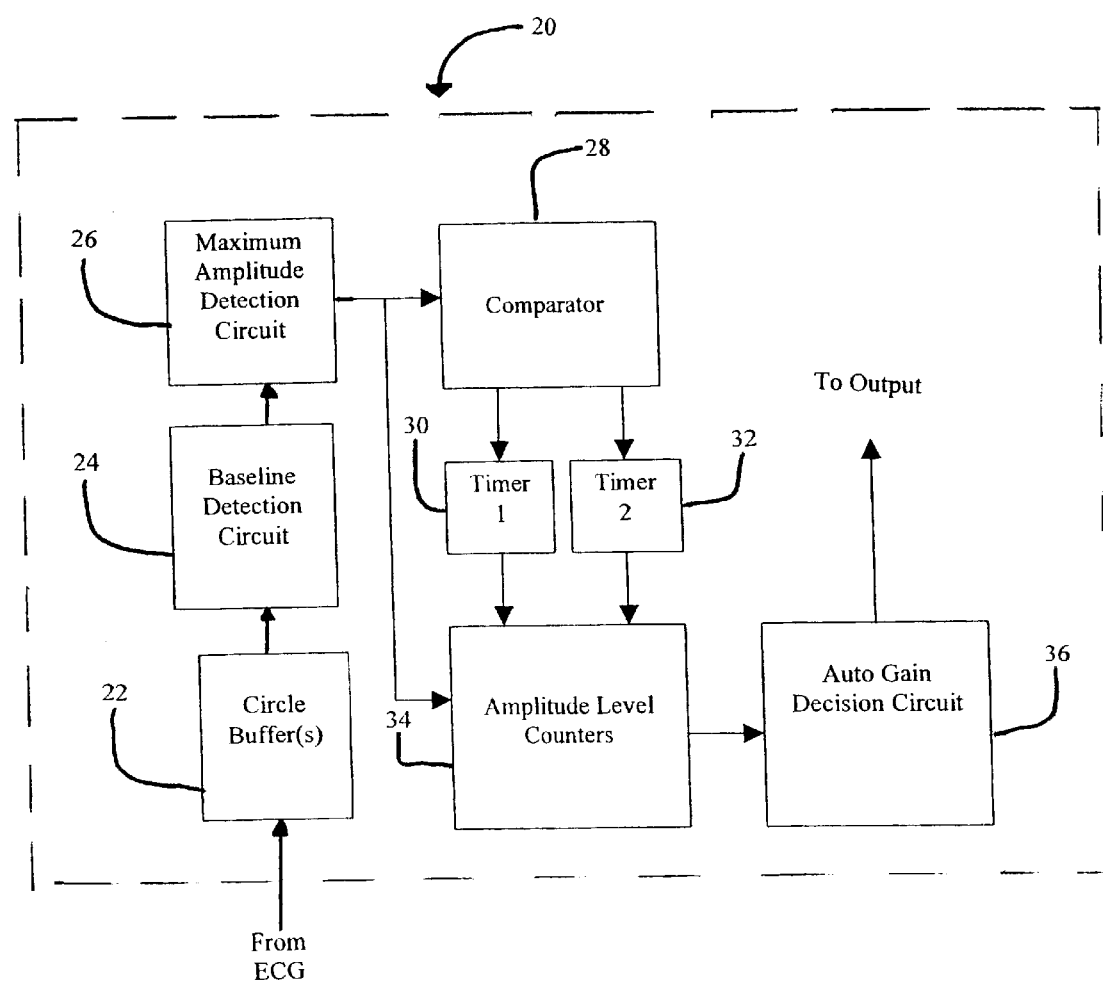
FIG. 2 is a block diagram illustrating an automatic gain control in accordance with the present invention.

An AGC 20 in accordance with the present invention is illustrated in FIG. 2. AGC 20 may be implemented by a microprocessor having appropriate software, using a conventional circuit or a combination of the two. AGC 20 uses at least one vector as the input to detect changes in the amplitude of the output waveform from ECG 10. Thus, AGC 20 is coupled to or integral with ECG device 10 to receive at least one vector and to control the amplitude of the output. AGC 20 uses an algorithm to determine whether or not to alter the gain setting for output device 18 based on the amplitude of the vectors or vectors. If the amplitude for a particular vector or vectors falls outside the prescribed range, AGC 20 changes the gain setting to maintain the output within the prescribed range. That is, if the output amplitude of output device 18 is too high AGC 20 reduces the gain setting or if the output amplitude is too low, AGC 20 increases the gain setting. The higher the amplitude of the ECG data, the numerically lower the ECG gain setting should be. For example, if the amplitude of the R wave is 1 mV, the gain is set to 10 mm/mV and, if the amplitude of R wave were to drop to 0.5 mV, the gain should be adjusted to 20 mm/mV. AGC 20 includes a plurality of gain settings. Typically, 5 gain settings, including: 20 mm/mV, 10 mm/mV, 5 mm/mV, 2 mm/mV and 1 mm/mV are used to adjust the amplitude of an ECG's output. For exemplary purposes, the following description discusses an AGC having five gain settings.

AGC 20 receives data from digital data processor 16, shown in FIG. 1, and determines whether or not to alter the gain. Typically, the data received by AGC 20 is decimated. The decimation of data minimizes the number of calculations and saves memory space. Typically, the data is decimated by a factor of two or more. The particular degree of decimation depends on the particular sampling rate of A/D converter 14. AGC 20 may be integrated into the ECG device 10, as shown in FIG. 1, or it may be a separate connectable component. Further, AGC 20 may be defeatable, allowing either manual or automatic adjustment of the gain. From the data, AGC 20 calculates a baseline and establishes a plurality of threshold amplitudes relative to the baseline. AGC 20 calculates amplitudes of at least one vector from the data received from the ECG. The amplitude of the at least one vector is compared with the thresholds. AGC 20 then determines whether or not to adjust the gain based on the comparison of the vectors' amplitude with the thresholds.

As shown in FIG. 2, AGC 20 may include at least one circle buffer 22, a baseline detection circuit 24, a maximum amplitude detection circuit 26, a comparator 28, a first timer 30, a second timer 32, a plurality of amplitude level counters 34 and a decision circuit 36. The data from digital data processor 16 in ECG device 10, shown in FIG. 1, is stored in cycle buffer 22. Typically, AGC 20 has between 1 to 12 circle buffers, one for each of the possible vectors used by the ECG device 10. Each circle buffer 22 receives the digitized data from its assigned vector and stores the data for discrete periods of time. Typically, cycle buffer 22 may store the data for a period of about one second.

Baseline detection circuit 24 uses the data stored in the cycle buffer to establish a baseline. Baseline detection circuit 24 includes first and/or second order differentiators, and accumulators for each vector. In operation, an exclusion threshold may be established in the circuit to detect anomalously high values and rapidly changing data. If the differentiated data is lower than the exclusion threshold, the vector sample will be added into accumulator. If the differentiated data is higher or equal to the exclusion threshold, the data is discarded. Discarding the anomalous data prevents the inappropriate raising or lowering of the baseline. The result is that only slow changing data is used for baseline detection and therefore, the baseline more accurately represents physiological changes in the patient. The baseline is calculated by dividing the value in the accumulator by the number of samples entered into the accumulator to obtain an average.

Maximum amplitude detection circuit 26 detects the vector with the highest amplitude from a particular set of stored data. Maximum amplitude detection circuit 26 calculates the difference between each vector and each vector's baseline which is representative of each vector's amplitude. From each vector's amplitude, maximum amplitude detection circuit 26 establishes the maximum absolute value for all vectors. The maximum value is absolute in that it typically includes values falling both above and below the baseline. The vector having the highest absolute value is used as input data to determine whether or not to alter the gain.

Comparator circuit 28, first timer 30, second timer 32 and amplitude level counter 34 cooperate to establish the gain values. Auto-gain decision circuit 36 uses the gain values to determine whether or not to increase or decrease the gain setting. Comparator 28 receives the input data from maximum amplitude detection circuit 28 and controls the timers. The timers establish the measurement window. Amplitude level counter 34 determines the highest threshold crossed during the measurement period and provides the information as a particular gain value to auto-gain decision circuit 36.

Comparator 28 controls the initiation of first timer 30. The comparator receives the input data from maximum amplitude detection circuit 26. The comparator compares the amplitude of the input data with an initiation threshold. The initiation threshold is chosen to prevent the first timer's initiation upon the ECG's sensing of minor artifacts. When the magnitude of the input data exceeds an initiation threshold, comparator circuit 28 starts the first timer 30.

Figure 3:
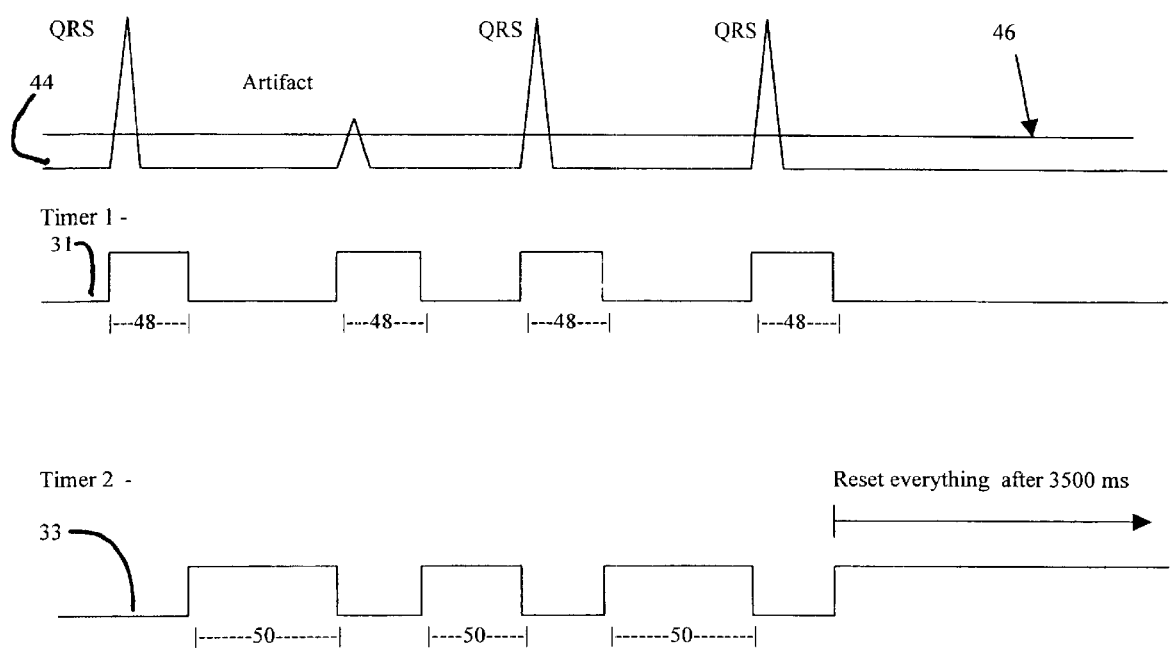
FIG. 3 illustrates by idealized waveforms the cooperation of the first and second timers.

FIG. 3 illustrates the cooperation of first timer 30 and second timer 32 along lines 31 and 33, respectively. The timers further cooperate with the amplitude of data from ECG 10 illustrated by waveform 44. When the amplitude excursion of the signal exceeds an initiation threshold 46, first timer 30 is started. The running of first timer 30 establishes a measurement window 48. Measurement window 48 is the period during which the gain value is established. Typically, first timer 30 is set for about 500 milliseconds to create a 500 millisecond measurement window 48. Five hundred milliseconds typically provide ample time to sense the input data's maximum amplitude after a depolarization event. In addition, the starting of first timer 30 stops and resets second timer 32. Second timer 32 is started by two events: initial system reset; and the first timer's expiration. Typically, second timer 32 has a duration of about 3500 millisecond. The 3500 millisecond period establishes the maximum void window 50 between measurement windows 48 without system reset. That is, if the input data does not cross the initiation threshold 46 for more than 3500 milliseconds, the second timer times out. Upon timing out, second timer 32 resets the system. Thus, first timer 30 and the second timer 32 work in opposition to one another.

Amplitude level counter 34 detects the amplitude of data during measurement window 48. Amplitude level counter 34 typically includes a counter for each of a set of possible gain values to be used by the decision circuit 36. Typically, amplitude level counter 34 includes five counters for five possible gain values. Each counter registers when the amplitude of the input data exceeds a corresponding gain threshold. For example, the five gain thresholds may correspond to the standard gain values as follows:

| Gain Values | Gain Thresholds |
| --- | --- |
| 20 mm/mV | 0.5 mV |
| 10 mm/mV | 1 mV |
| 5 mm/mV | 2 mV |
| 2 mm/mV | 5 mV |
| 1 mm/mV | 10 mV |

Thus, the counters record the number of times the input data crosses a particular gain threshold during a measurement window established by the timers. Amplitude level counter 34 is configured to provide the highest gain threshold crossed as a gain value to auto-gain decision circuit 36. Amplitude level counter 34 is reset upon the expiration of either first timer 30 or second timer 32.

In operation, comparator circuit 28, first timer 30, second timer 32 and amplitude level counter 34 run through a plurality of cycles to generate a plurality of gain values for auto-gain decision circuit 36. After system reset, the first input data to cross the initiation threshold starts first timer 30 and stops and resets second timer 32. During this first measurement window, amplitude level counter 34 determines the first gain value. Upon timing out, first timer 30 stops and is reset to zero and the second timer is started. The second input data to cross initiation threshold 46 again starts first timer 30 and stops and resets second timer 32. During the second measurement window, amplitude level counter 34 determines the second gain value. The process continues until the desired number of gain values have been established. Typically, auto gain decision circuit 36 uses four gain values. Therefore, after a fourth measurement window, auto gain decision circuit 36 uses the four gain values to determine the appropriate gain setting. Once the desired number of gain values is determined and provided to the auto-gain decision circuit the system is reset and a new set of gain values is determined.

Auto-gain decision circuit 36 uses a set of rules or algorithm based on the plurality of gain values to determine the appropriate gain setting. The decision circuit may implement a variety of rules to determine whether or not to alter the gain. The following rules 1 and 2 work in concert and are provided for exemplary purposes.

Rule 1: If at least two of four gain values are equal to one another and at least three of the gain values are greater than the current gain setting then a new gain setting will be set the same as the two or more equivalent higher gain values.

Rule 2: If at least two of four gain values are equal to one another and at least three of the gain values are lower than the current gain setting then a new gain setting will be set the same as the two or more equivalent lower gain values.

One skilled in the art, upon review of the disclosure, will recognize that various rules and sets of rules may be established to determine whether or not the gain is to be altered.

It can be seen then that there is provided an automatic gain control for controlling the gain for an output device of an ECG. The automatic gain control receives data and stores the data in discrete periods of time, typically in a circle buffer. A baseline is established for the data and an amplitude established relative to the baseline. A maximum amplitude from the discrete period of time is then established and the maximum amplitude is compared to a set of thresholds representative of a set of gain values. The auto-gain decision circuit then uses the gain values corresponding to the thresholds to establish the appropriate gain setting for the output. As data continually cycles through the cycle buffer the apparatus and method continuously update the gain setting to provide the appropriate amplitude for the output.

The invention has been described in considerable detail to provide those skilled in the art with information needed to apply the novel principles of the present invention. However, upon review of the disclosure, those skilled in the art will appreciate that many variations of the present invention are possible, that the invention can be carried out using different equipment and processes, and that the various modifications to physical details and operating functions can be effected without departing from the scope of the invention. Thus, the description is intended as an example only, and is not intended to limit the invention, except as set forth in the claims.

What is claimed is:

1. A method for automatic adjustment of gain, comprising:
   receiving data representative of at least one vector from an electrocardiogram device;
   determining an amplitude of the vector;
   comparing the amplitude with a plurality of thresholds to establish a gain value for the vector; and
   adjusting a gain setting based on the gain value.

2. A method, as in claim 1, further comprising:
   establishing a baseline value for the vector, wherein the amplitude is determined relative to the baseline value.

3. A method, as in claim 2, wherein data above an exclusion threshold is excluded from the establishing the baseline value.

4. A method, as in claim 1, further wherein the relationship of the gain value is input into an algorithm to determine the gain setting.

5. A method, as in claim 1, wherein determining the amplitude of the vector occurs during a measurement window.

6. A method, as in claim 1, wherein the measurement window is initiated upon the amplitude of the vector crossing an initiation threshold.

7. A method, as in claim 1, wherein data indicative of the vector from the electrocardiogram device is decimated.

8. An device for auto-gain control, comprising:
   at least one circle buffer for receiving data indicative of output of an electrocardiograph device;
   a baseline detection circuit for establishing a baseline from the data;
   a maximum amplitude detection circuit for establishing the maximum amplitude of the data relative to the baseline;
   a comparator circuit for comparing a plurality of amplitudes from the maximum amplitude detection circuit with a plurality of thresholds; and
   a decision circuit for determining a gain setting from a relationship between the plurality of amplitudes with the plurality of thresholds.

* * * * *